(12) United States Patent
Swan et al.

(10) Patent No.: US 12,251,844 B2
(45) Date of Patent: Mar. 18, 2025

(54) MULTIPURPOSE SHEARS

(71) Applicant: Cygnus Medical LLC, Plain City, UT (US)

(72) Inventors: Alexander Stephen Swan, Plain City, UT (US); Cameron J Nielson, Orem, UT (US)

(*) Notice: Subject to any disclaimer, the term of this patent is extended or adjusted under 35 U.S.C. 154(b) by 251 days.

(21) Appl. No.: 17/579,191

(22) Filed: Jan. 19, 2022

(65) Prior Publication Data

US 2022/0234226 A1   Jul. 28, 2022

Related U.S. Application Data

(60) Provisional application No. 63/140,611, filed on Jan. 22, 2021.

(51) Int. Cl.
| | |
|---|---|
| *B26B 13/00* | (2006.01) |
| *B26B 13/04* | (2006.01) |
| *B26B 13/08* | (2006.01) |
| *B26B 13/12* | (2006.01) |
| *B26B 13/26* | (2006.01) |
| *A01G 3/025* | (2006.01) |
| *A61B 17/28* | (2006.01) |

(52) U.S. Cl.
CPC .......... *B26B 13/005* (2013.01); *B26B 13/04* (2013.01); *B26B 13/08* (2013.01); *B26B 13/12* (2013.01); *B26B 13/26* (2013.01); *A01G 3/0251* (2013.01); *A61B 17/2812* (2013.01)

(58) Field of Classification Search
CPC ....... B26B 13/00; B26B 13/005; B26B 13/04; B26B 13/06; B26B 13/08; B26B 13/12; B26B 13/22; B26B 13/26; A61B 17/3201

USPC ..................... D8/57; 30/254, 255
See application file for complete search history.

(56) References Cited

U.S. PATENT DOCUMENTS

| | | | | |
|---|---|---|---|---|
| 127,207 | A * | 5/1872 | Young | B26B 13/005 |
| | | | | 30/255 |
| 201,475 | A * | 3/1878 | Wright | B26B 13/005 |
| | | | | 30/255 |
| 293,182 | A * | 2/1884 | Loockerman | B26B 13/22 |
| | | | | 30/255 |
| 377,637 | A * | 2/1888 | Pauls | B26B 13/005 |
| | | | | 30/255 |
| 425,560 | A * | 4/1890 | Badger | B26B 13/005 |
| | | | | 30/255 |

(Continued)

FOREIGN PATENT DOCUMENTS

| | | | | | |
|---|---|---|---|---|---|
| FR | | 334855 A | * | 1/1904 | ........... B26B 13/005 |
| FR | | 510398 A | * | 12/1920 | ........... B26B 13/005 |

(Continued)

*Primary Examiner* — Jason Daniel Prone
(74) *Attorney, Agent, or Firm* — Accelerate IP LLC

(57) ABSTRACT

Foldable, multipurpose shears can have a pair of shearing blades, each blade having a sharp side and a blunt side. The blades are connected to handles via a hinge, and the handles have one side that is straighter and another side that is more rounded or irregularly shaped. One of the blades includes a backward facing hook on the blade's blunt side. Additionally, the blunt side may have partially sharpened serrations. The blades can fold about the hinge for easier transport and storage and the shears are configured so that the hook does not extend past the handles when folded.

8 Claims, 13 Drawing Sheets

(56) References Cited

U.S. PATENT DOCUMENTS

| | | | | |
|---|---|---|---|---|
| 429,000 A * | 5/1890 | Badger | B26B 11/00 | |
| | | | 30/255 | |
| 631,403 A * | 8/1899 | Metcalf | B26B 13/22 | |
| | | | 30/255 | |
| 1,090,130 A * | 3/1914 | Borgetti | B26B 13/005 | |
| | | | 30/255 | |
| 1,093,432 A * | 4/1914 | Kalina | B26B 13/005 | |
| | | | 30/255 | |
| 1,354,807 A * | 10/1920 | Dietrich | B26B 13/005 | |
| | | | 30/231 | |
| 1,409,978 A * | 3/1922 | Smith | B26B 13/005 | |
| | | | 30/255 | |
| 1,524,694 A * | 2/1925 | Di Maio | B26B 13/005 | |
| | | | 30/255 | |
| 1,904,399 A * | 4/1933 | Balthaser | A61B 17/3201 | |
| | | | 30/233 | |
| 2,126,699 A * | 8/1938 | Florian | B26B 13/005 | |
| | | | 30/255 | |
| D118,280 S * | 12/1939 | Hausmann | D8/57 | |
| 2,192,725 A * | 3/1940 | Williams | B26B 13/005 | |
| | | | 30/255 | |
| 2,568,605 A * | 9/1951 | Bennett | B26B 13/005 | |
| | | | 30/255 | |
| 2,588,939 A * | 3/1952 | Selander | B26B 13/005 | |
| | | | 30/255 | |
| 2,952,912 A * | 9/1960 | Crawford | B26B 13/005 | |
| | | | 30/255 | |
| 3,766,648 A * | 10/1973 | Chundelak, Jr. | B26B 13/005 | |
| | | | 30/255 | |
| 3,781,992 A * | 1/1974 | Barr | B26B 13/005 | |
| | | | 30/255 | |
| 3,987,542 A * | 10/1976 | Visco | B26B 13/12 | |
| | | | D8/57 | |
| D285,166 S * | 8/1986 | Lee | D8/57 | |
| 4,658,456 A * | 4/1987 | Tsai | B26B 13/22 | |
| | | | 7/137 | |
| 4,791,725 A * | 12/1988 | Amagaya | B26B 13/12 | |
| | | | 30/255 | |
| 4,794,692 A * | 1/1989 | Wang | B26B 13/22 | |
| | | | 30/255 | |
| 4,924,572 A * | 5/1990 | Vogel | B26B 13/12 | |
| | | | 30/253 | |
| D333,416 S * | 2/1993 | Brown, Jr. | D8/57 | |
| 5,357,678 A * | 10/1994 | Wei | B26B 13/005 | |
| | | | 30/162 | |
| 5,485,677 A * | 1/1996 | Seber | B26B 3/06 | |
| | | | 30/294 | |
| 5,526,571 A * | 6/1996 | Linden | B26B 13/005 | |
| | | | 30/255 | |
| 5,722,171 A * | 3/1998 | Schmidt | B26B 13/12 | |
| | | | 30/255 | |
| D437,197 S * | 2/2001 | Ohno | D8/57 | |
| D460,334 S * | 7/2002 | Carpenter | D8/57 | |
| D549,335 S * | 8/2007 | Junck | D8/57 | |
| D557,096 S * | 12/2007 | Wu | D8/57 | |
| D594,723 S * | 6/2009 | Kim | D8/57 | |
| 7,810,242 B1 * | 10/2010 | Lynch | B26B 13/285 | |
| | | | 30/259 | |
| D723,161 S * | 2/2015 | Goldstein | D24/148 | |
| 8,959,777 B2 * | 2/2015 | Forman | B26B 13/22 | |
| | | | 30/146 | |
| 9,187,114 B2 * | 11/2015 | Covel | B62B 13/005 | |
| D758,817 S * | 6/2016 | Covel | D8/57 | |
| D771,450 S * | 11/2016 | Maille | D8/57 | |
| D787,287 S * | 5/2017 | Martinez | D8/57 | |
| 10,569,434 B2 * | 2/2020 | Covel | B26B 13/005 | |
| D955,199 S * | 6/2022 | Kao | D8/55 | |
| D972,387 S * | 12/2022 | He | D8/57 | |
| D983,000 S * | 4/2023 | Luo | D8/57 | |
| D983,633 S * | 4/2023 | Fujita | D8/57 | |
| D992,390 S * | 7/2023 | Swan | D8/57 | |
| D1,027,591 S * | 5/2024 | Ishida | D8/57 | |
| D1,045,554 S * | 10/2024 | Monk | D8/57 | |
| 2010/0083509 A1 * | 4/2010 | Grist | B26B 13/12 | |
| | | | 30/341 | |
| 2012/0195027 A1 * | 8/2012 | Russ | B26B 13/06 | |
| | | | 362/119 | |
| 2014/0190015 A1 * | 7/2014 | Forman | B26B 13/08 | |
| | | | 30/254 | |

FOREIGN PATENT DOCUMENTS

| | | | | |
|---|---|---|---|---|
| FR | 605887 A * | 6/1926 | | B26B 13/005 |
| GB | 191503654 A * | 3/1916 | | B26B 13/005 |
| GB | 116221 A * | 6/1918 | | B26B 13/005 |
| GB | 2487402 A * | 7/2012 | | B26B 13/005 |

* cited by examiner

MULTIPURPOSE SHEARS

CROSS-REFERENCE TO RELATED APPLICATIONS

This application claims benefit from currently U.S. Provisional Application No. 63/140,611 titled "Multipurpose Shears" and having a filing date of Jan. 22, 2021, all of which is incorporated by reference herein.

FIELD OF THE INVENTION

The present specification relates to a shearing device for use in the medical field, as well as camping, hunting, and fishing and more particularly a multipurpose collapsible shearing device.

BACKGROUND OF THE INVENTION

Cutting tools such as shears, scissors or multipurpose tools are common tools for cutting a variety of materials ranging from clothing to textiles and plastics. The size and shape of the cutting tool depends on the material and the thickness of the material being cut. Shears are key pieces of equipment for medical personnel including but not limited to emergency medical response, rescue and veterinary professionals. In many instances, the scissors utilized by such medical personnel have been developed for specific applications such as emergency medical technician ("EMT") shears, bandage and veterinary scissors. EMT shears, for example, are designed to cut through heavy fabrics such as denim or seatbelt material. Veterinary scissors, another type of specialized scissors, having one smooth blade and one serrated blade, are designed for cutting through cartilage and soft bone.

Shears can also be a key piece of equipment for hunters and trappers. An animal harvested in the field by a hunter must be quickly skinned and eviscerated and it is common practice for hunters to skin and clean the animal at the site of the kill. The hunter cuts through the layer of hide, hair and other connective tissue so that it can be peeled away from the meat. After the hide and hair are removed, another cut is made through the layer of meat to permit it to be separated from the visceral lining containing the viscera.

It is advantageous to cut the hide from the inside of the animal toward the outside to avoid pushing hair, dirt, and other contaminants into the meat of the animal. At the same time, it is important to avoid puncturing the viscera of the animal to prevent the contents of the stomach or bowel from contaminating the meat. To achieve both of these criteria, hunting knives will frequently include a "gut hook" or "skinning gut hook." The gut hook includes a hook-shaped, backwardly facing, slot on the back side of the knife blade that has a non-sharpened portion to pull the hide away from the viscera and a sharpened portion to cut the hide. The hook is pushed through the layer to be cut and drawn toward the user doing the cutting so that the hide or meat is cut by the sharpened interior of the slot.

In medicine, hunting, and many other pursuits, convenient storage and storage space are other important concerns for any tools that are used to carry out the pursuit. Multi-tools and folding knives, saws and other implements have been developed in an attempt to address this concern. For blades including a partially sharpened hook, the extending hook portion of the blade can be inconvenient to sheath, store, or fold.

Therefore, there is a need for a foldable cutting implement that can be safely and conveniently stored.

BRIEF SUMMARY OF THE INVENTION

In one or more embodiments a system of foldable shears is provided, comprising a first blade having a first sharp side and a first blunt side, the first blade coupled to a first handle about a hinge, the first handle having a first inner face, a first outer face, a first inner edge and a first outer edge. A second blade coupled to a second handle via the hinge, the second handle having a second outer face, a second inner face, a second inner edge, and a second outer edge. A recess on the first blunt side forming a backward facing hook. The first blade and the second blade are configured to fold about the hinge to substantially overlap with the first handle and the second handle such that at least a portion of the first inner edge is adjacent to at least a portion of the second inner edge and at least a portion of the first outer edge is adjacent to at least a portion of the second outer edge. The first blunt side of the first blade substantially aligns with a straight portion of the second inner edge of the second handle when the shears are folded. The straight portion defines a plane, and the hook does not extend beyond the plane when the shears are folded.

The second handle further comprises a first projection extending inwardly from the second handle and wherein the first projection resides at least partially in the recess when the shears are folded. The first blade comprises a first blade stop, the second blade comprises a second blade stop, the first inner face comprises a spring operated first blade lock and the second handle comprises a spring operated second blade lock, wherein the first blade lock contacts the first blade stop to prevent the first blade from rotating past a desired point relative to the first handle and wherein the second blade lock contacts the second blade stop to prevent the second blade from rotating past a desired point relative to the second handle. The first blunt side is at least partially serrated. The first blade comprises a first cavity and the second blade comprises a correspondingly shaped second cavity configured to operate as an oxygen wrench. The at least one of the handles comprises a hex tool insert. A portion of the second handle is a spring latch to allow the second handle to operate as a carabiner. The first handle and the second handle comprise an angled shape like an L-shape for improved ergonomics.

A system of foldable shears, comprising a first blade having a first inner surface and a first outer surface, the first blade coupled to a first handle about a hinge, the first handle having a first inner face, a first outer face, a first inner edge and a first outer edge. A second blade having a second inner surface and a second outer surface, the second blade coupled to a second handle via the hinge, the second handle having a second outer face, a second inner face, a second inner edge, and a second outer edge. A recess on the first blade forming a backward facing hook. The first blade and the second blade are configured to fold about the hinge to substantially overlap with the first handle and the second handle such that the first inner edge is adjacent to the second inner edge and the first outer edge is adjacent to the second outer edge. The first inner face comprises a first prong configured to reside within a first groove in the first outer surface limiting the range of rotation of the first handle relative to the first blade. The second inner surface comprises a second prong configured to reside within a second groove on the first inner surface limiting the range of rotation of the second blade relative to the first blade. The second inner face comprises a third prong configured to reside within a third groove on the second outer surface limiting the range of rotation of the second handle relative to the second blade. The second inner edge defines a plane and the hook does not extend beyond the plane when the shears are folded.

A method of assembling foldable shears can comprise providing a first handle having a first prong and a first recess accommodating a first inner face, a first blade having an outer surface with first groove and an inner surface with a second groove, a second blade having an inner surface with a prong and an outer surface with a third groove, and a second handle have a prong and a second recess accommodating a second inner face. Assembling the first handle, first blade, second blade and second handle about a hinge pin such that the first prong resides in the first groove, the second prong resides in the second groove, and the third prong resides in the third groove. The first blade comprises a first blade stop, the second blade comprises a second blade stop, the first inner face comprises a spring operated first blade lock and the second handle comprises a spring operated second blade lock, and wherein the first handle, first blade, second blade, and second handle are assembled such the first blade lock contacts the first blade stop and the second blade lock contacts the second blade stop to prevent rotation of the first blade relative to the first handle and the second blade relative to the second handle.

The first blade further comprises a backward facing hook and the second handle comprises an inward facing projection and wherein the method further comprises assembling the first handle, first blade, second blade and second handle about the hinge pin such that the inward facing projection resides in the hook. The first handle can comprise a first inner face, a first outer face, a first inner edge and a first outer edge, the second handle comprises a second outer face, a second inner face, a second inner edge, and a second outer edge, wherein the second inner edge has a straight portion that defines a plane, the method further comprising assembling the first handle, first blade, second blade and second handle about the hinge pin such that the hook does not extend beyond the plane when the shears are folded.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventors are fully aware that they can be their own lexicographers if desired. The inventors expressly elect, as their own lexicographers, to use only the plain and ordinary meaning of terms in the specification and claims unless they clearly state otherwise and then further, expressly set forth the. Absent such clear statements of intent to apply a "special" definition, it is the inventor's intent and desire that the simple, plain, and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of 35 U.S.C. § 112 (f). Thus, the use of the words "function," "means" or "step" in the Detailed Description or Description of the Drawings or claims is not intended to somehow indicate a desire to invoke the special provisions of 35 U.S.C. § 112 (f), to define the invention. To the contrary, if the provisions of 35 U.S.C. § 112 (f) are sought to be invoked to define the inventions, the claims will specifically and expressly state the exact phrases "means for" or "step for" and will also recite the word "function" (i.e., will state "means for performing the function of . . . , without also reciting in such phrases any structure, material or act in support of the function. Thus, even when the claims recite a "means for performing the function of molding a . . . , step for performing the function of molding a . . . ," if the claims also recite any structure, material or acts in support of that means or step, or that perform the recited function, then it is the clear intention of the inventors not to invoke the provisions of 35 U.S.C. § 112 (f). Moreover, even if the provisions of 35 U.S.C. § 112 (f) are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

Additional features and advantages of the present specification will become apparent to those skilled in the art upon consideration of the following detailed description of the illustrative embodiment exemplifying the best mode of carrying out the invention as presently perceived.

BRIEF DESCRIPTION OF THE DRAWINGS

These and other features, aspects, and advantages of the present specification will become better understood in light of the following description, appended claims, and accompanying drawings where:

Elements and acts in the figures are illustrated for simplicity and have not necessarily been rendered according to any particular sequence or embodiment.

DETAILED DESCRIPTION

In the following description, and for the purposes of explanation, numerous specific details are set forth to provide a thorough understanding of the various aspects of the invention. It will be understood, however, by those skilled in the relevant arts, that the present invention may be practiced without these specific details. In other instances, known structures and devices are shown or discussed more generally to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Figure 1:
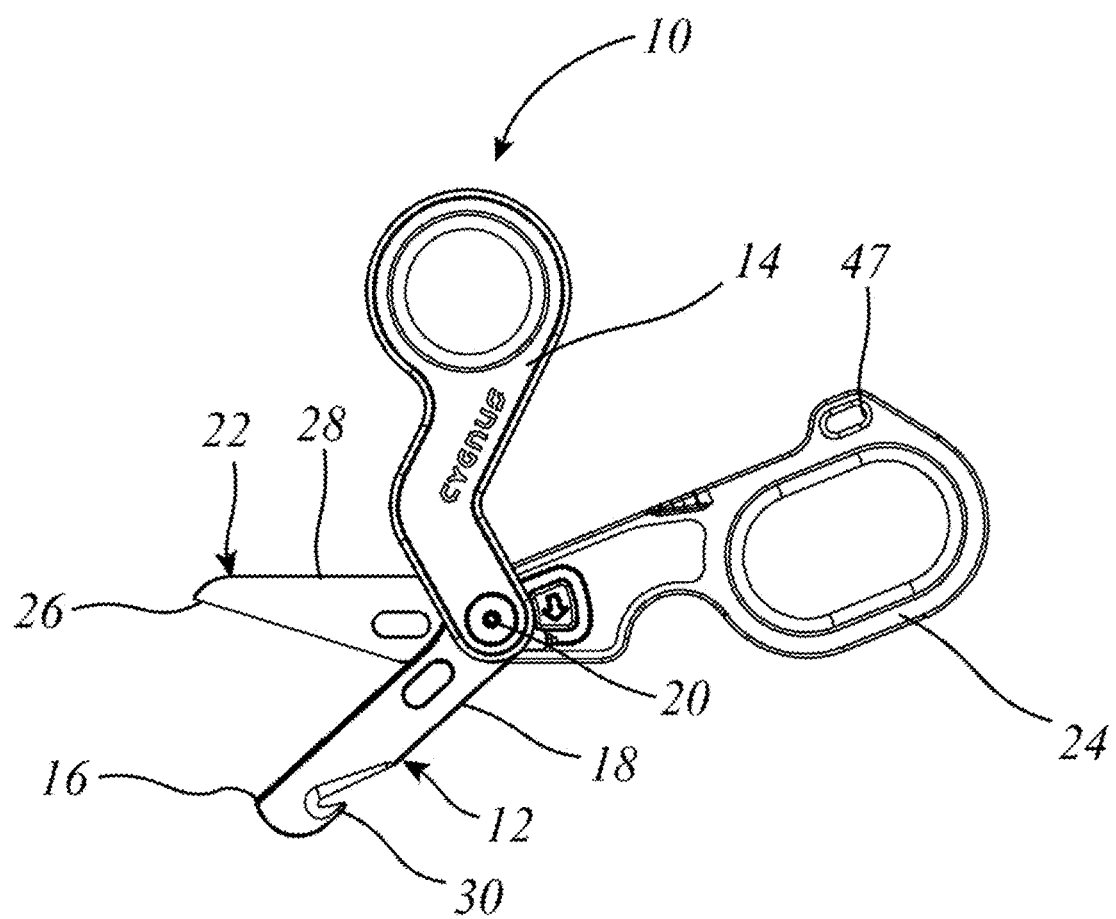
FIG. 1 is a top view of the multipurpose shears in accordance with one, or more embodiments in the unfolded, open position.
Figure 2:
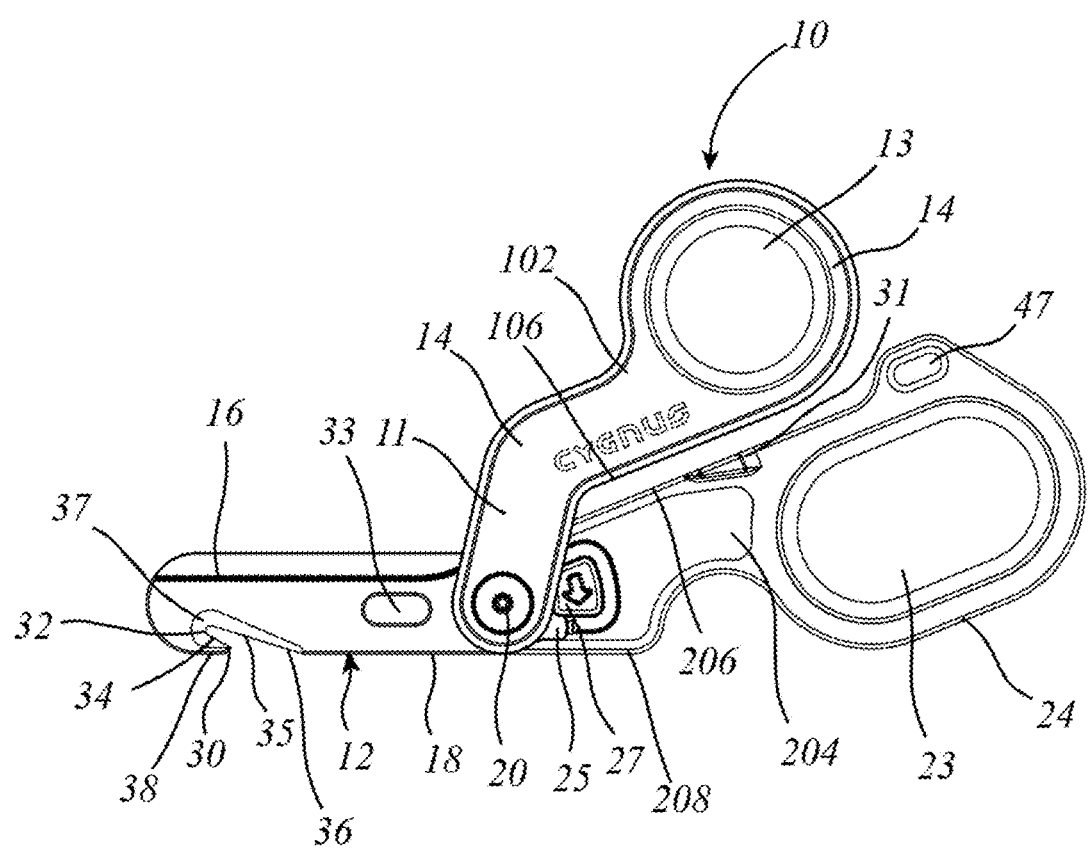
FIG. 2 is a front isometric view of the multipurpose shears in accordance with one, or more embodiments in the unfolded closed position.
Figure 3:
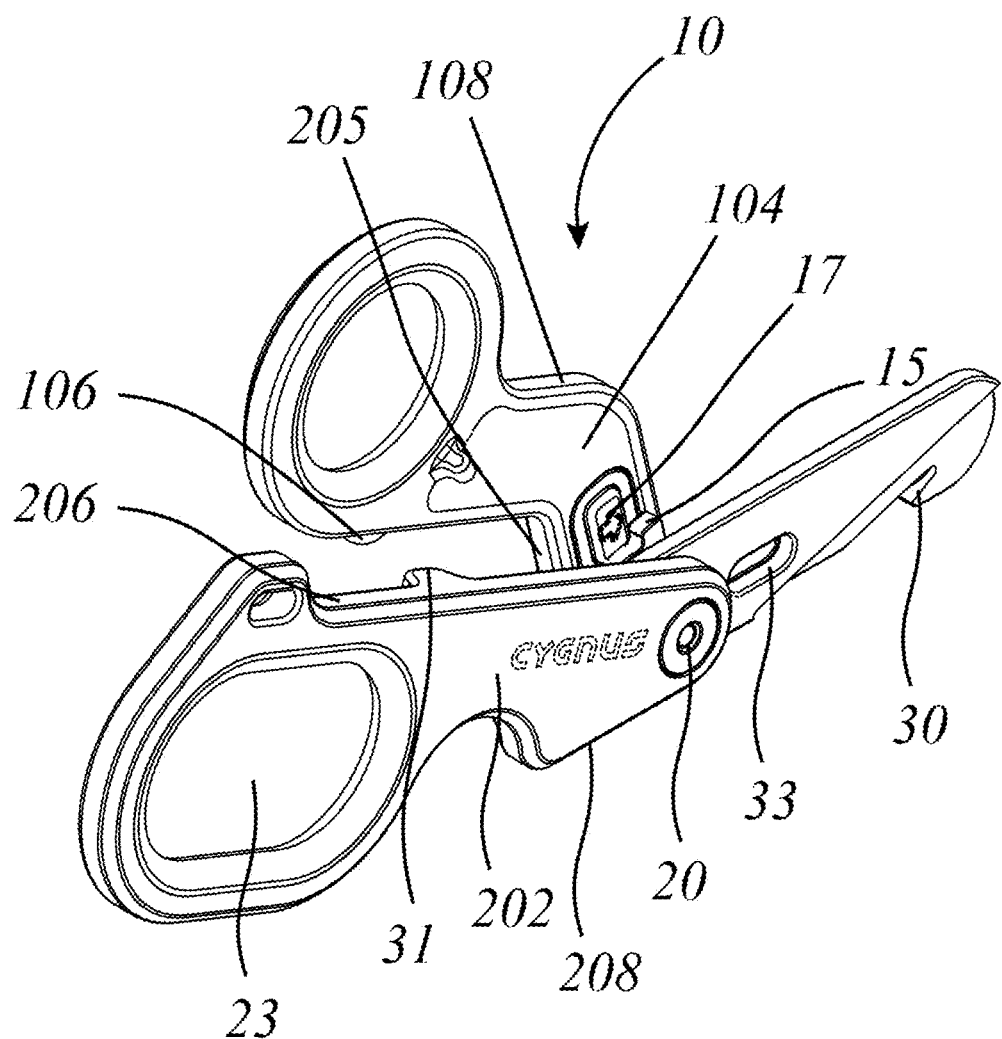
FIG. 3 is a rear isometric view of the multipurpose shears in accordance with one, or more embodiments in the unfolded, closed position.
Figure 4A:
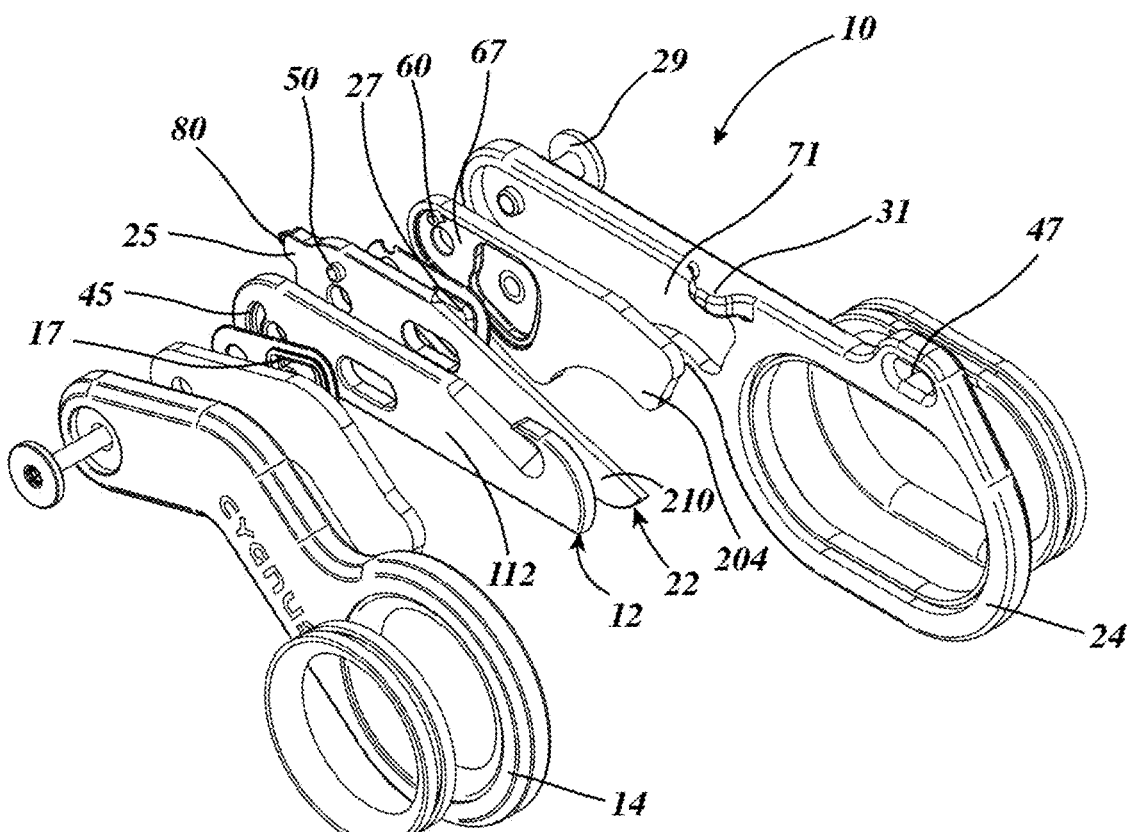
FIG. 4*a* is an exploded view of the multipurpose shears in accordance with one or more embodiments.

Referring initially to FIGS. 1-3, a set of folding shears 10 is provided having a first blade 12 and a second blade 22 coupled to a first handle 14 and a second handle 24 at a hinge 20. The first blade 12 has a first substantially sharpened side 16 and a first blunt side 18 and the second blade 22 has a second sharpened side 26 and second blunt side 28. The blunt sides 18, 28 may include some sharpened portion such as a partially or fully sharpened hook 30, which can be a backward facing hook, and at least one of the blades has a serrated portion 19, as shown in FIG. 4c. In one embodiment, the first blade 12 has a hook 30 that has a sharpened crook 32 and a blunted extension 34 and in other embodiments the hook 30 can be omitted from the first blade 12.

In one embodiment the hook 30 is formed on the first blunt side 18 of the folding shears 10. A recess 35 is formed from a portion of the first blunt side 18 by an angled portion 36 from the first blunt side 18. The recess 35 then has a looped portion 37 that loops around and then meets the blunted extension 34 that comes to a point 38 of the hook 30 that is in line with the rest of the first blunt side 18. At least a portion of the angled portion 36 and the looped portion 37 is sharpened to allow the hook 30 to cut. The point 38 may be sharp or may be rounded for safety and to avoid having the hook 30 catch on clothing or other objects near the site being cut.

When the handles 14, 24 are closed together, the blades 12, 22 of the folding shears 10 are also closed together and can be partially overlapping. When the handles 14, 24 are moved away from each other, the blades 12, 22 of the folding shears 10 similarly move away from each other rotating about a hinge 20. Referring specifically to FIG. 1, the folding shears 10 are shown in the open position and referring specifically to FIG. 2 the folding shears are shown in the closed position. When the first handle 14 is moved in an upward direction, the connection at the hinge 20 enables the first blade 12 to move in the downward direction, away from the second blade 22. Similarly, moving the second handle 24 in the downward direction, the connection at the hinge 20 enables the second blade 22 in the upward direction away from the first blade 12. The second handle 24 may have a stop 31 extending inwardly from the second handle.

The first handle 14 has a first outer face 102, a first inner face 104, a first inner edge 106, and a first outer edge 108. Similarly, the second handle 24 has a second outer face 202, a second inner face 204, a second inner edge 206, and a second outer edge 208.

The first handle 14 may be shaped to include a first hole 13 to accommodate a user's thumb while the second handle 24 is configured include a second hole 23 to accommodate a plurality of a user's fingers, or vice versa. Alternatively, both handles 14, 24 may be uniformly shaped to accommodate either a thumb or a plurality of a user's fingers. The handles 14, 24 may extend straight from the blades 12, 22, or may include an angle change 11, at the hinge 20 for improved ergonomics. As shown most clearly in FIG. 6, the folding shears 10 have essentially four adjacent planes, with the handles 14, 24 residing in the two outer planes and the blades 12, 22 in the two inner planes. The plane of the first handle 14 is adjacent to the plane of the first blade 12, and the plane of the second handle 24 is adjacent to the plane of the second blade 22. The planes of the blades 12, 22 are adjacent to each other.

Figure 4B:
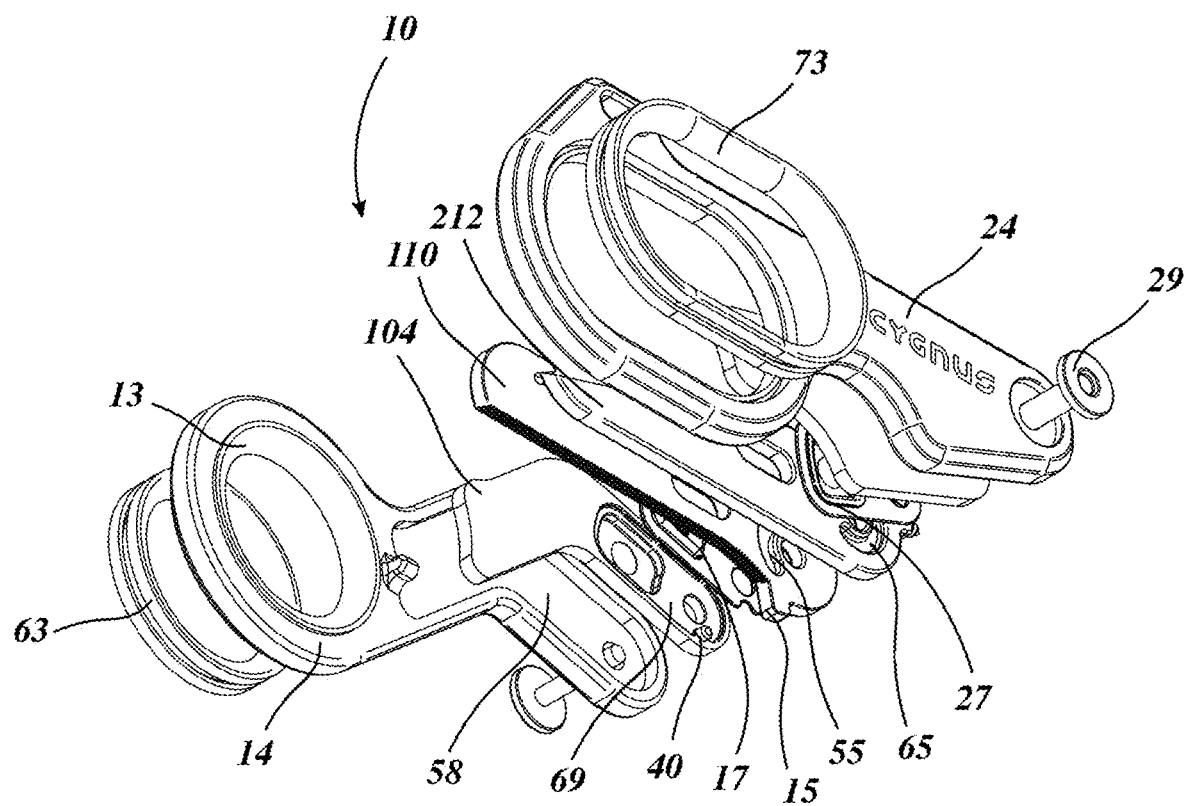
FIG. 4*b* is an exploded view of the multipurpose shears in accordance with one or more embodiments.
Figure 4C:
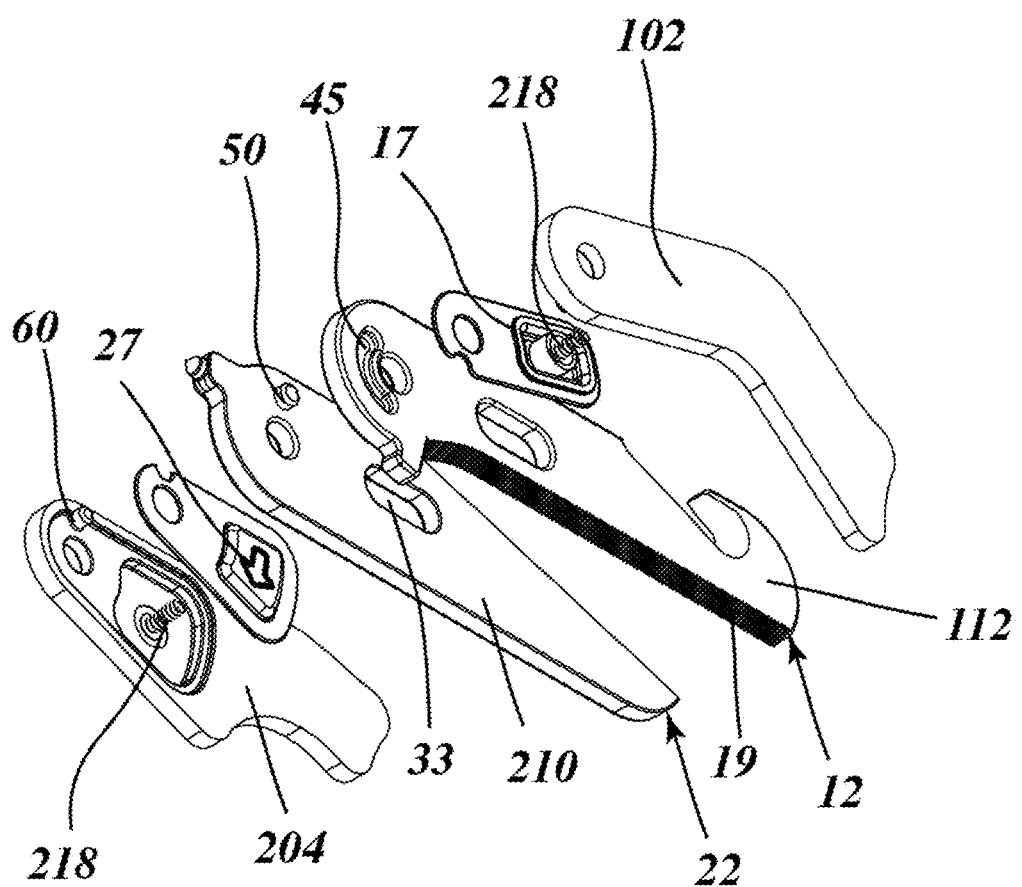
FIG. 4*c* is an exploded view of the multipurpose shears in accordance with one or more embodiments.

Referring to FIG. 3 and FIG. 4b, the first blade 12 has a first blade stop 15 coupled to the first blade 12 and a second blade stop 25 coupled to the second blade 22. A first blade lock 17 is situated on the first inner face 104 and spring operated inwardly away from the first handle 14. The first blade stop 15 comes into contact against the first blade lock 17, preventing the first blade 12 from pivoting past a certain point defined by the location of the first blade stop 15 and the first blade lock 17. As best shown in FIG. 2, a second blade lock 27 is situated on the second inner face 204 and spring operated inwardly away from the second handle 24. The blade locks 17, 27 may be spring operated by an internal spring 218 or by the face of the blade lock resisting deformation toward the handle, as shown in FIG. 4c. The second blade stop 25 comes into contact against the second blade lock 27, preventing the second blade 22 from pivoting past a certain point defined by the location of the second blade stop 25 and the second blade lock 27.

The first blade 12 and the second blade 22 can comprise a first cutout 33 located in the substantially the same position on the first blade and the second blade. Alternatively, or additionally, a first handle cutout 47 may be included in the first handle 14 or the second handle 24. The first cutout 33 or first handle cutout 47 can be used as a wrench to open and close oxygen tanks, or other objects that require use of a wrench.

Referring to FIGS. 4a-4d, the first blade 12 can further comprise a first groove 45 on the outer side of the first blade 12 and a second groove 55 on the inner side of the first blade 12. The depth of the grooves 45, 55 can be about half of the thickness of the first blade 12. In a particular embodiment, the first groove 45 and the second groove 55 substantially overlap, forming a cavity through the entire thickness of the first blade 12. The first inner face 104 can comprise a first prong 40 configured to reside in the first groove 45. The first prong 40 can rotate within the first groove's 45 path limiting the rotation of the first handle 14 relative to the first blade 12.

The second blade 22 can comprise a second prong 50 configured to reside in the second groove 55. The second prong 50 can rotate within the second groove's path limiting the rotation of the second blade 22 relative to the first blade 12. The second blade 22 can further comprise a third groove 65 and the second inner face 204 can comprise a third prong 60 that can rotate within the third groove 65 limiting the rotation of the second blade relative to the second handle 24.

The first blade 12 and the first handle 14 can move and lock into position independently from the second blade 22 and the second handle 24. The second blade stop 25 can comprise a blunt end 80 for breaking glass or the like. The first handle 14 can further comprise a first inner ring 63 and the second handle 24 can comprise a second inner ring 73 wherein the inner rings can be a rubber, plastic, or the like material to provide comfort to the user's fingers while in use. In other embodiments, the second blade 22 can have two grooves that interact with each other as described above with the first blade's first groove 45 and second groove 55 and the first blade 12 can have one groove.

In some embodiments the first inner face 104 can further comprise a first window 69 for the first blade lock 17 and the second inner face 204 can comprise a second window 67 for the second blade lock 27. The first handle 14 can have a first recess 58 to which the first outer face 102 can be connected, attached, or pressed, retaining the first outer face 102 within the first handle 14. The second handle 24 can have a second recess 71 to which the second inner face 204 can be connected, attached, or pressed, capturing the first inner face 104 within the second handle. In other embodiments the first handle 14 and the first inner face 104 can be one piece or multiple pieces and the second handle 24 and the second inner face 204 can be one piece or multiple pieces.

Figure 5:
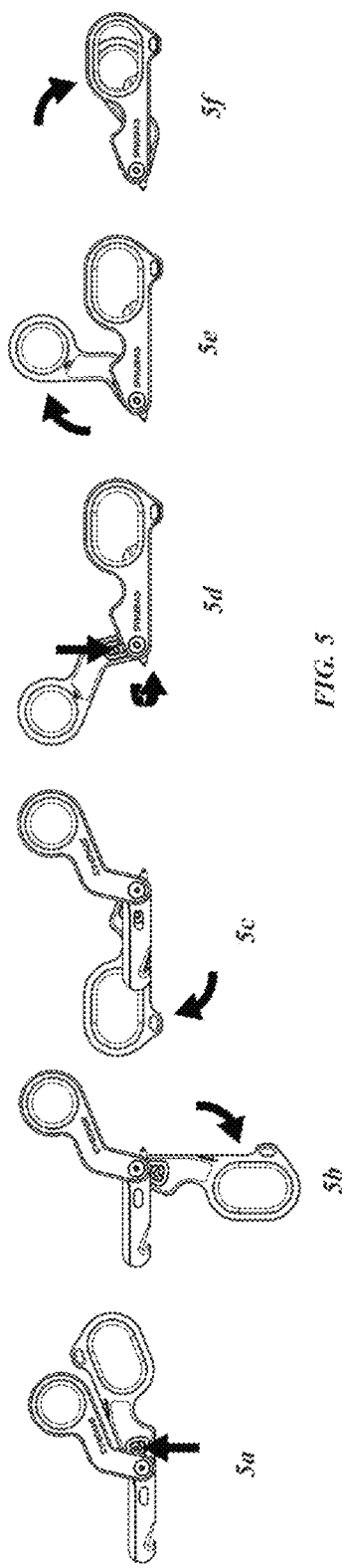
FIG. 5 is a top sequential view of the multipurpose shears in accordance with one or more embodiments.

Referring to FIG. 5, to fold the shears, the second blade lock 27 is depressed allowing the second blade stop 25 to pass over the second blade lock 27 and rotate in a downward direction as shown in FIG. 5b. The first blade lock 17 may then be depressed allowing the first blade stop 15 to pass over the first blade lock 17 and rotate in an upward direction as shown in FIG. 5d.

Figure 6:
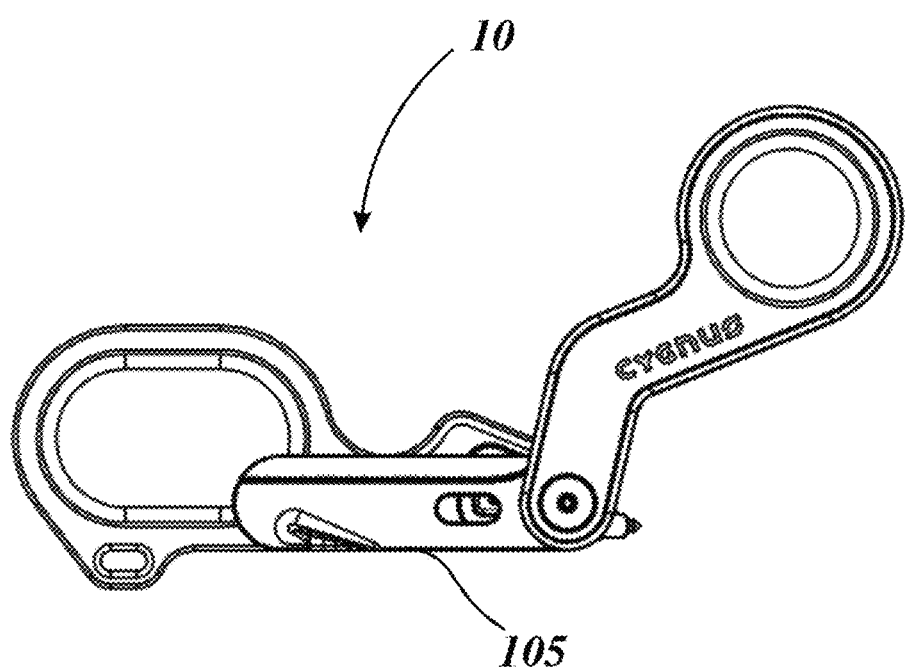
FIG. 6 is a front isometric view of the multipurpose shears in accordance with one, or more embodiments.
Figure 7:
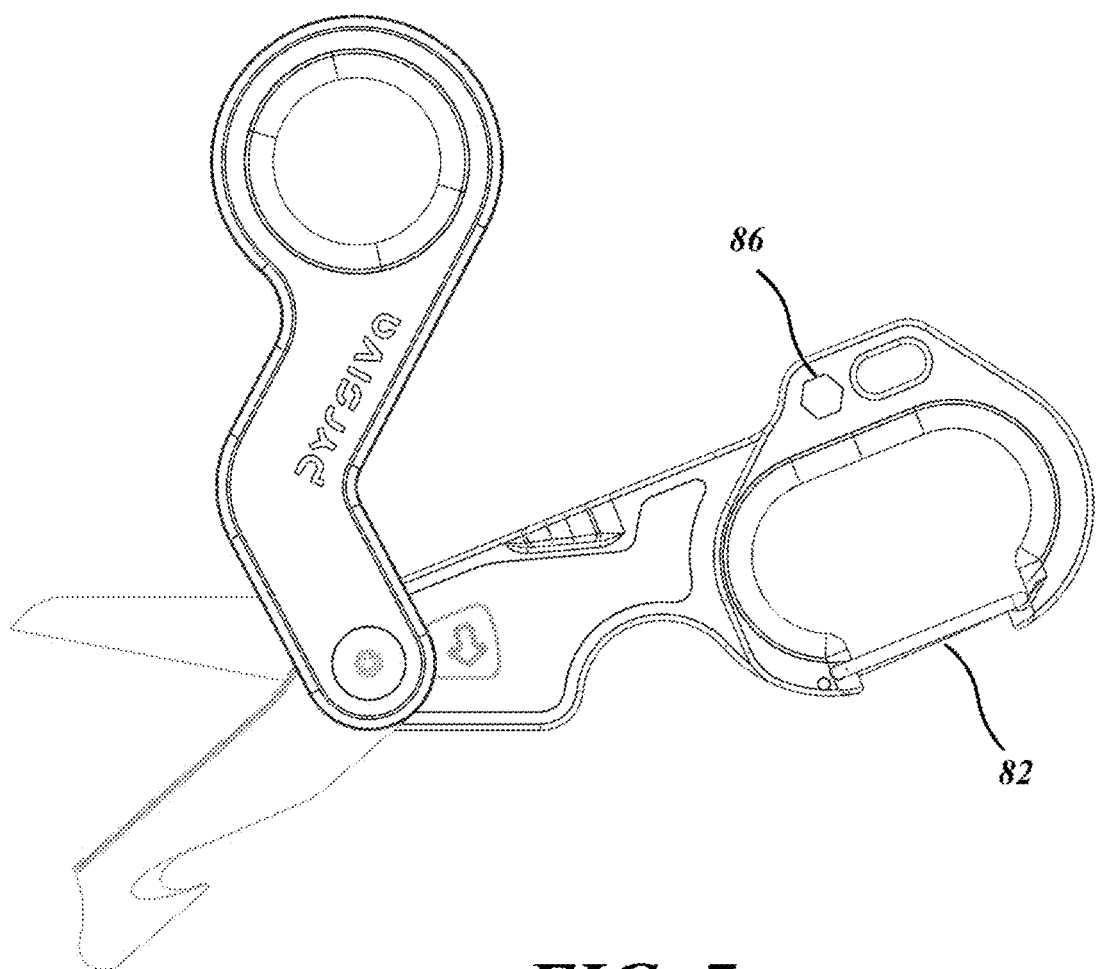
FIG. 7 is a top view of the multipurpose shears in accordance with one, or more embodiments in the unfolded, open position.
Figure 8:
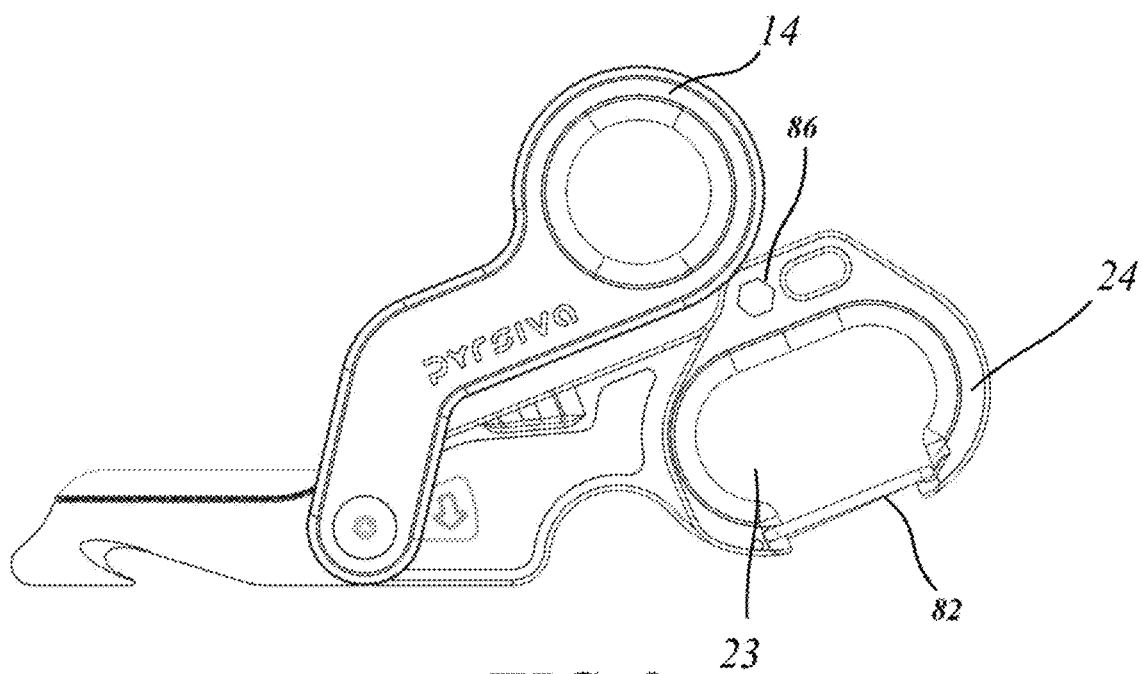
FIG. 8 is a top view of the multipurpose shears in accordance with one, or more embodiments in the unfolded closed position.
Figure 9:
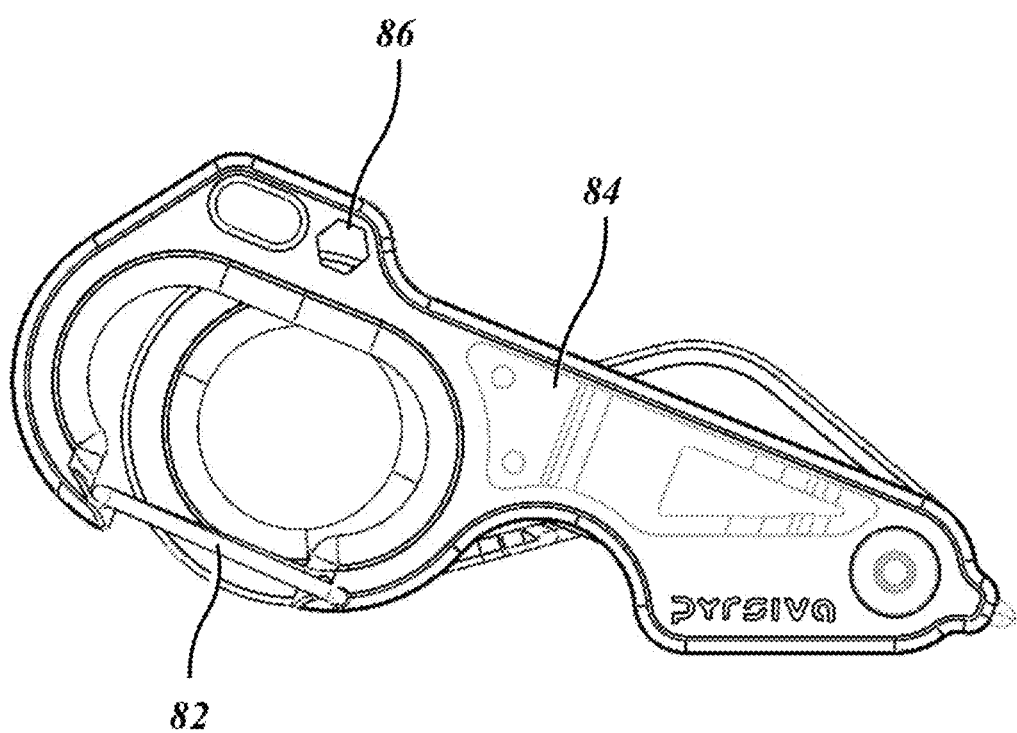
FIG. 9 is a top view of the multipurpose shears in accordance with one, or more embodiments in the folded position.
Figure 10:
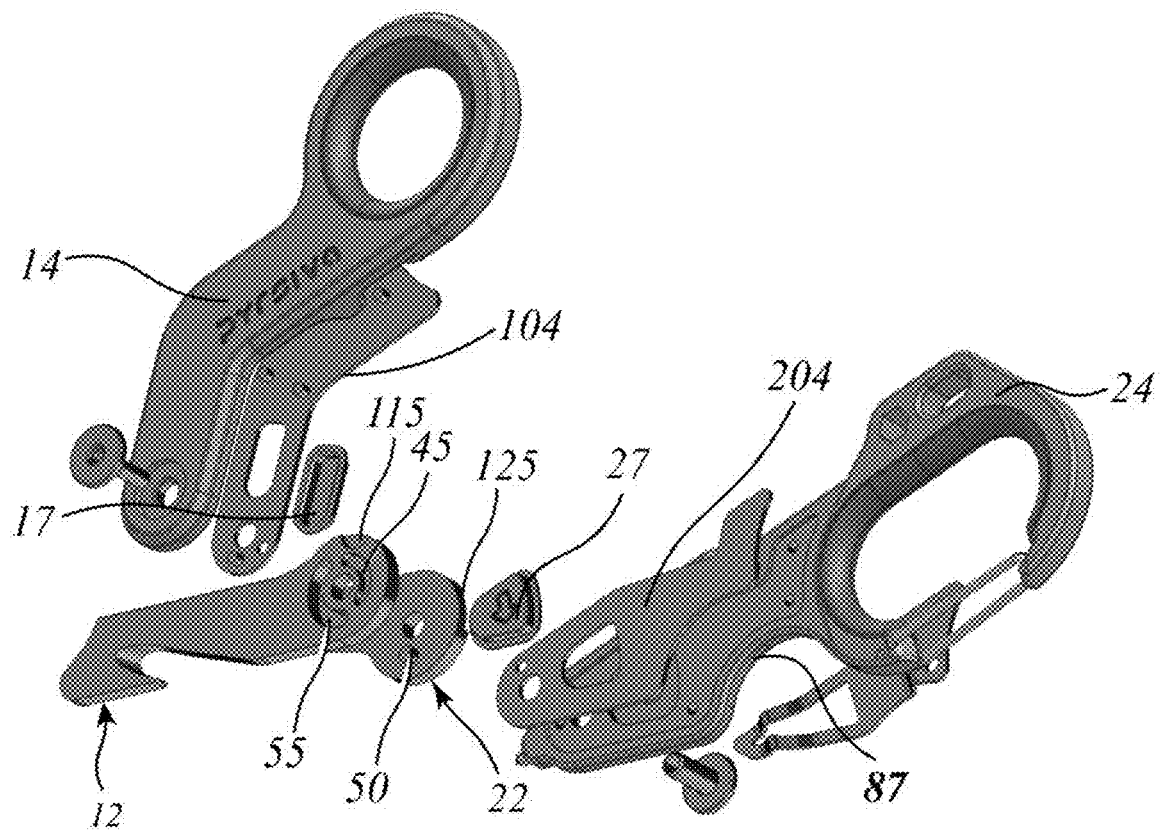
FIG. 10 is an exploded view of the multipurpose shears in accordance with one or more embodiments.

The folding shears 10 are in the fully folded position when the stop 31 resides at least partially within the recess 35. In a particular embodiment, the stop 31 substantially fills the portion of the first blunt side 18 that is recessed such that the first blunt side 18 and the stop 31 form a substantially complete straight line 105 as shown in FIG. 6.

Figure 4D:
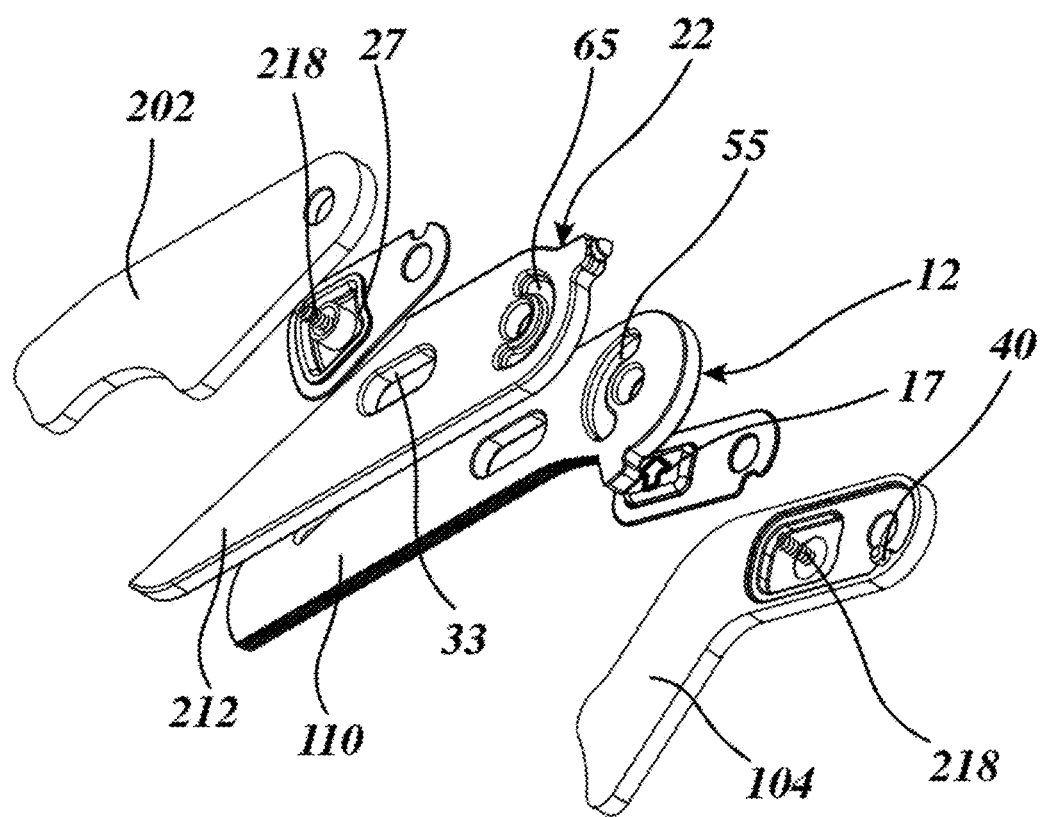
FIG. 4*d* is an exploded view of the multipurpose shears in accordance with one or more embodiments.

Referring to FIGS. 7-10, a portion of the second handle 24 defining the second hole 23 may be replaced with a spring latch 82 allowing the second hole 23 to operate as a carabiner. A pocket clip 84 may be coupled to one of the handles 14, 24 and one of the handles 14, 24 may also include an insert 86 configured to accept a hex tool. The first blade 12 has a first blade stop 115 and the second blade 22 has a second blade stop 125. The first blade lock 17 is situated on the first inner face 104 and spring operated inwardly away from the first handle 14 and a portion of the first blade lock 17 fits into the first blade stop 115 when the folding shears 10 are unfolded, locking the first blade 12 in position relative to the first handle 14. A second blade lock 27 is situated on the second inner face 204 and spring operated inwardly by the internal spring 218, as shown in FIG. 4d, away from the second handle 24. A portion of the second blade lock 27 fits into the second blade stop 125 when the folding shears 10 are unfolded, locking the second blade 22 in position relative to the second handle 24.

A method of assembling foldable shears, the method comprising providing a first handle 14 having a first prong 40 and a first recess 58 accommodating a first inner face 104, a first blade 12 having a first outer surface 112, as shown in FIG. 4a, with first groove 45 and an inner surface 110 with a second groove 55, as shown in FIGS. 4b and 4d, a second blade 22 having a second inner surface 210 with a second prong 50 and a second outer surface 212 with a third groove 65, and a second handle 24 having a third prong 60 and a second recess 71 accommodating a second inner face 204. Assembling the first handle, first blade, second blade 22 and second handle about a hinge pin 29, as shown in FIGS. 4a and 4b, such that the first prong 40 resides in the first groove 45, the second prong 50 resides in the second groove 55, and the third prong 60 resides in the third groove 65. The first blade 12 comprises a first blade stop 15, the second blade 22 comprises a second blade stop 25, the first inner face 104 comprises a spring operated first blade lock 17 and the second handle 24 comprises a spring operated second blade lock 27, and wherein the first handle 14, first blade 12, second blade 22, and second handle 24 are assembled such the first blade lock 17 contacts the first blade stop 15 and the second blade lock 27 contacts the second blade stop 25 to prevent rotation of the first blade 12 relative to the first handle 14 and the second blade 22 relative to the second handle 24.

The first blade 12 further comprises a hook 30 and the second handle 24 comprises an inward facing projection 87 and wherein the method further comprises assembling the first handle 14, first blade 12, second blade 22, and second handle 24 about the hinge pin 29 such that the inward facing projection resides next to the hook 30. The first handle 14 can comprise a first inner face 104, a first outer face 102, a first inner edge 106 and a first outer edge 108, the second handle 24 comprises a second outer face 202, a second inner face 204, a second inner edge 206, and a second outer edge 208, wherein the second inner edge 206 has a straight portion 205 that defines a plane, the method further comprising assembling the first handle 14, first blade 12, second blade 22, and second handle 24 about the hinge pin 29 such that the hook 30 does not extend beyond the plane when the shears are folded.

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. For example and not by way of limitation, the hook 30 may be present in the first blade 12 or the second blade 22 without materially departing from the principles of the subject matter of the invention. Lastly, the terminology used herein is for the purpose of describing particular embodiments only and is not intended to limit the scope of the present disclosure, which is defined solely by the claims. Accordingly, embodiments of the present disclosure are not limited to those precisely as shown and described.

Certain embodiments are described herein, including the best mode known to the inventors for carrying out the methods and devices described herein. Of course, variations on these described embodiments will become apparent to those of ordinary skill in the art upon reading the foregoing description. Accordingly, this disclosure includes all modifications and equivalents of the subject matter recited in the claims appended hereto as permitted by applicable law. Moreover, any combination of the above-described embodiments in all possible variations thereof is encompassed by the disclosure unless otherwise indicated herein or otherwise clearly contradicted by context.

What is claimed is:

1. A system of foldable shears, comprising:
a first blade having a first inner surface and a first outer surface, the first blade coupled to a first handle about a hinge, the first handle having a first inner face, a first outer face, a first inner edge portion and a first outer edge portion;
a second blade having a second inner surface and a second outer surface, the second blade coupled to a second handle via the hinge, the second handle having a second outer face, a second inner face, a second inner edge portion, and a second outer edge portion;
a recess on the first blade forming a backward facing hook;
wherein the first blade and the second blade are configured to fold about the hinge from a fully open position to a fully folded position wherein when opening from the fully folded position to the fully open position the first handle rotates relative to the first blade through a first range of rotation and the second handle rotates relative to the second blade through a second range of rotation;
wherein the first blade and the first handle rotate relative to the second blade and the second handle through a cutting range or rotation when the shears are in the fully open position;
wherein the first inner face comprises a first prong configured to reside within a first groove in the first outer surface wherein the first prong rotates around an axis within the first groove which limits the first range of rotation of the first handle relative to the first blade;
wherein the second inner surface comprises a second prong configured to reside within a second groove on the first inner surface wherein the second prong rotates around an axis within the second groove which limits the cutting range of rotation;
wherein the second inner face comprises a third prong configured to reside within a third groove on the second outer surface wherein the third prong rotates around an axis within the third groove which limits the second range of rotation of the second handle relative to the second blade; and
wherein a straight portion of the second inner edge defines a plane and the hook does not extend beyond the plane when the shears are folded.

2. The foldable shears according to claim 1, wherein the second handle further comprises a first projection extending inwardly from the second handle and wherein the first projection resides at least partially in the recess when the shears are in the fully folded position.

3. The foldable shears according to claim 1, wherein the first blade comprises a first blade stop, the second blade comprises a second blade stop, the first inner face comprises a spring operated first blade lock and the second handle comprises a spring operated second blade lock, wherein the first blade lock contacts the first blade stop to prevent the first blade from rotating relative to the first handle when the shears are in the fully open position or in the fully folded position, and wherein the second blade lock contacts the second blade stop to prevent the second blade from rotating relative to the second handle when the shears are in the fully open position or in the fully folded position.

4. The foldable shears according to claim 1 wherein at least one side of at least one of the blades is at least partially serrated.

5. The foldable shears according to claim 1 wherein the first blade comprises a first cavity and the second blade comprises a correspondingly shaped second cavity to accept an oxygen valve and operate as an oxygen wrench.

6. The foldable shears according to claim 1, the second handle comprises a x-shaped cutout to accept a hex-shaped object to rotate the hex-shaped object.

7. The foldable shears according to claim 1, wherein a portion of the second handle is a spring latch to allow the second handle to operate as a carabiner.

8. The foldable shears according to claim 1 wherein the first handle has an angled shape.

* * * * *